US012727850B2

(12) United States Patent
Wei et al.

(10) Patent No.: US 12,727,850 B2
(45) Date of Patent: Sep. 8, 2026

(54) AUGMENTED IMAGING FOR VALVE REPAIR

(71) Applicant: Evalve, Inc., Santa Clara, CA (US)

(72) Inventors: Michael F. Wei, Redwood City, CA (US); Chad J. Abunassar, San Francisco, CA (US)

(73) Assignee: Evalve, Inc., Santa Clara, CA (US)

(*) Notice: Subject to any disclaimer, the term of this patent is extended or adjusted under 35 U.S.C. 154(b) by 870 days.

(21) Appl. No.: 17/858,719

(22) Filed: Jul. 6, 2022

(65) Prior Publication Data

US 2023/0009891 A1 Jan. 12, 2023

Related U.S. Application Data

(60) Provisional application No. 63/219,561, filed on Jul. 8, 2021.

(51) Int. Cl.
*A61B 8/08* (2006.01)
*A61B 8/12* (2006.01)
*A61B 34/20* (2016.01)

(52) U.S. Cl.
CPC .............. *A61B 8/0883* (2013.01); *A61B 8/12* (2013.01); *A61B 34/20* (2016.02)

(58) Field of Classification Search
CPC ....... A61B 34/20; A61B 8/065; A61B 8/0883; A61B 8/12; A61B 8/463; A61B 8/488; A61B 8/5223; A61B 8/5238; A61B 8/5261
See application file for complete search history.

(56) References Cited

U.S. PATENT DOCUMENTS

| | | | | |
|---|---|---|---|---|
| 7,604,646 | B2 | 10/2009 | Goldfarb | |
| 8,057,493 | B2 | 11/2011 | Goldfarb | |
| 8,560,968 | B1 * | 10/2013 | Nair ...................... | G16H 40/63 715/810 |
| 2005/0256398 | A1 * | 11/2005 | Hastings ............... | A61B 34/73 600/410 |

(Continued)

FOREIGN PATENT DOCUMENTS

| | | | |
|---|---|---|---|
| EP | 3692925 | A1 | 8/2020 |
| JP | 2009045081 | A * | 3/2009 |
| WO | 2014001955 | A1 | 1/2014 |

OTHER PUBLICATIONS

“Cardiac Cycle”, Wikipedia, The Free Encyclopedia, accessed on Nov. 15, 24, url: https://en.wikipedia.org/wiki/Cardiac_cycle (Year: 2024).*

(Continued)

*Primary Examiner* — Katherine L Fernandez
(74) *Attorney, Agent, or Firm* — SLEMAN & LUND LLP

(57) ABSTRACT

Systems and methods for augmenting image data during heart valve repair procedures, such as transcatheter mitral valve repair (TMVr) or transcatheter tricuspid valve repair (TTVr). Image data may be obtained from an imaging device, and may be output to a display with one or more reference markers overlaid on the image data to simplify the visual data. Image data may be augmented or replaced with the reference markers. In some cases, reference markers may provide information about objects that are difficult to see in the image data. In other cases, the reference markers may provide clinical recommendations or feedback.

18 Claims, 9 Drawing Sheets

(56) References Cited

U.S. PATENT DOCUMENTS

| | | | | |
|---|---|---|---|---|
| 2006/0029269 | A1* | 2/2006 | Matsuoka | G06T 11/008 382/132 |
| 2008/0221442 | A1* | 9/2008 | Tolkowsky | A61B 6/5217 378/22 |
| 2010/0069757 | A1* | 3/2010 | Yoshikawa | A61B 5/02007 600/454 |
| 2011/0092819 | A1* | 4/2011 | Takimoto | G01S 7/52066 600/454 |
| 2013/0150710 | A1* | 6/2013 | Zentgraf | A61B 8/461 600/424 |
| 2013/0150717 | A1* | 6/2013 | Sato | A61B 8/466 600/443 |
| 2013/0172758 | A1* | 7/2013 | de Marchena | A61B 8/0883 600/464 |
| 2015/0148679 | A1* | 5/2015 | Thiele | G01S 15/8979 600/454 |
| 2015/0294454 | A1* | 10/2015 | Nempont | A61B 6/5247 382/128 |
| 2017/0151027 | A1* | 6/2017 | Walker | A61B 34/37 |
| 2021/0137680 | A1 | 5/2021 | Kizuka | |
| 2021/0145574 | A1 | 5/2021 | Childs | |
| 2021/0145583 | A1 | 5/2021 | Abunassar | |
| 2021/0186698 | A1 | 6/2021 | Abunassar | |
| 2021/0315695 | A1 | 10/2021 | Van Hoven | |
| 2021/0393404 | A1 | 12/2021 | Ketai | |
| 2022/0054132 | A1 | 2/2022 | Ketai | |
| 2022/0117737 | A1 | 4/2022 | Abunassar | |

OTHER PUBLICATIONS

Dormer et al., "Image Guided Mitral Valve Replacement: Registration of 3D Ultrasound and 2D X-ray Images", Proc SPIE INt Soc Opt Eng., Feb. 2020, pp. 1-17. (Year: 2020).*

English translation of JP-2009045081 (Year: 2009).*

Emmeline E Calkoen et al: "Characterization and quantification of dynamic eccentric regurgitation of the left atrioventricular valve after atrioventricular septal defect correction with 4D Flow cardiovascular magnetic resonance and retrospective valve tracking", Journal of Cardiovascular Magnetic Resonance, Biomed Central Ltd, London UK, vol. 17, No. 1, Feb. 19, 2015, 9 pages.

* cited by examiner

AUGMENTED IMAGING FOR VALVE REPAIR

CROSS-REFERENCE TO RELATED APPLICATIONS

This application claims the benefit of the filing date of U.S. Provisional Patent Application No. 63/219,561, filed Jul. 8, 2021, the disclosure of which is hereby incorporated by reference herein.

BACKGROUND

The present disclosure relates generally to methods and systems for imaging during minimally invasive interventional treatment for repairing a malfunctioning mitral valve or tricuspid valve within the heart.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which commonly occurs in the mitral and tricuspid valves.

Valve regurgitation is characterized by retrograde flow from the left or right ventricle of a heart through an incompetent mitral or tricuspid valve, respectively, into the left or right atrium, respectively. During a normal cycle of heart contraction (systole), the valve acts as a check valve to prevent flow of blood back into the atrium. In this way, the blood is pumped into the aorta or pulmonary artery, respectively. Regurgitation of the valve can significantly decrease the pumping efficiency of the heart, placing the patient at risk of severe, progressive heart failure.

One way of correcting valve regurgitation is by transcatheter delivery of an implant that facilitates full closure of the valve during each heart contraction cycle. Transcatheter delivery can be a complicated process requiring a surgeon to pay close attention to many inputs. Furthermore, many of the inputs can be difficult to interpret, especially while in the process of performing the transcatheter delivery procedure. For instance, typical imagery for transcatheter delivery may include trans-esophageal echocardiography (TEE) or transthoracic echocardiography (TTE). However, the echocardiography feedback is typically faint, grainy, shadowy and difficult to visualize in contrast to the implant. Additionally, due to the cardiac cycle and movement or flutter of each valve leaflet, there is no static point or position that may be fixated upon in order to assess placement of the implant and whether the implant has grasped the leaflet correctly. Due to the difficulties in interpreting echocardiography during the procedure, it may also be difficult for the surgeon to decide on an accurate target for the implant in order to minimize regurgitation or make an accurate prediction of success. As such, implantation becomes a trial-and-error process with a steep learning curve, which in turn can increase length of the procedure as well as risks to the patient.

Accordingly, it would be advantageous for a surgeon to be provided with useful imagery in a clear and straightforward fashion in order to simplify the delivery and implantation process and to flatten the learning curve and remove as much guesswork as possible from the procedure.

BRIEF SUMMARY

The present disclosure generally describes techniques and programs for augmenting image data typically viewed during heart valve repair procedures, such as transcatheter mitral valve repair (TMVr) or transcatheter tricuspid valve repair (TTVr). The augmented image data may include image data obtained from an imaging device augmented with one or more reference markers to simplify the collected image data. In some cases, aspects of the image data may be replaced with the reference markers to further improve visual understandability and clarity. In some cases, reference markers may provide information about objects that are difficult to see in the image data. In other examples, the reference markers may provide clinical recommendations or feedback.

One aspect of the disclosure is directed to an apparatus including one or more processors and memory in communication with the one or more processors. The memory contains instructions configured to cause the one or more processors to: receive, from a first imaging device, first image data of a plurality of image frames of a target heart valve of a subject, wherein the first image data indicates blood flow through the target heart valve; determine, from the first image data, each of a direction and a magnitude of a regurgitant flow through the target heart valve based on one or more of a jet width, a jet area, or a flow convergence region width; generate a reference marker indicating each of the direction and magnitude of the regurgitant flow; and output, to one or more image display devices, the first image data and the generated reference marker overlaid over the image frame in a position and orientation that indicates a position and the direction of the regurgitant flow.

In some examples, the instructions may be configured to cause the one or more processors to calculate autocorrelated flow data from the plurality of image frames, and determine the direction and magnitude of the regurgitant flow based on the autocorrelated data, whereby the generated reference marker is representative of autocorrelated flow data over a period of multiple cardiac cycles of the subject.

In some examples, the direction of the regurgitant flow may be indicated by a first property of the reference marker, and the magnitude of the regurgitant flow may be indicated by a second property of the reference marker. The reference marker may be an arrow, the direction of the regurgitant flow may be indicated by a direction of the arrow, and the magnitude of the regurgitant flow may be indicated by one of a color or length of the arrow. Additionally or alternatively, the instructions may be configured to cause the one or more processors to determine, from the first image data, a range of the regurgitant flow through the heart valve, and the generated reference marker may indicate the range by a third property of the reference marker.

In some examples, the first imaging device may be one of a trans-esophageal echocardiography (TEE) imaging device or a trans-thoracic echocardiography (TTE) imaging device.

In some examples, the first image data may include color Doppler data, and the instructions may be configured to cause the one or more processors to output the first image data without the color Doppler data.

In some examples, the instructions may be configured to cause the one or more processors to receive a user input indicating a desired image output mode from among: color Doppler data without reference markers, reference markers without color Doppler data, or both color Doppler data and reference markers, and output the first image data according to the user input.

In some examples, the first image data may be received from a first angle, and the instructions may be configured to cause the one or more processors to receive second image data of a target heart valve from a second angle different from the first angle, register the first image data with the second image data, generate a second reference marker based on the second image data, and output, to one or more image display devices, the first image data and the generated second reference marker overlaid over the image frame, whereby a position of the second reference marker in the image data is based on registration of the first image data with the second image data. The target heart valve may be the subject's mitral valve, the first angle may be from a trans-esophageal view, the second angle may be from a short-axis base view, and the second reference marker may identify one of the subject's left atrium, right atrium or superior vena cava. Alternatively, the target heart valve may be the subject's mitral valve, the first angle may be from a trans-esophageal view, the second angle may be from a four-chamber view, and the second reference marker may identify a height from a transeptal crossing to the mitral valve.

In some examples, the first image data of the target heart valve may be within an image plane, and the instructions may be configured to cause the one or more processors to, in response to a user input indicating to detect leaflet edges, transmit, to the first imaging device, an instruction to obtain offset image data in an offset image plane parallel to the image plane and offset by a predetermined distance, receive the offset image data, detect an edge of a leaflet of the target heart valve from the offset image data, interpolate, from the offset image data, a position of the edge of the leaflet in the image plane, generate an edge reference marker indicating the edge of the leaflet in the image plane, and output, to one or more image display devices, the first image data and the generated edge reference marker overlaid over the image frame, whereby a position of the edge reference marker in the first image data corresponds to the interpolated position of the edge of the leaflet.

In some examples, the instruction to obtain offset image data may instruct the first imaging device to obtain the offset image data on both sides of the image plane, the received offset image data may include first offset image data from an offset plane on a first side of the image plane and second offset image data from an offset plane on an opposite second side of the image plane, and the instructions may be configured to cause the one or more processors to interpolate the position of the edge of the leaflet in the image plane based on a combination of the first offset image data and the second offset image data.

In some examples, the instructions may be configured to cause the one or more processors to receive a device user input indicating a device present in the first image data, select, from a library of computer-generated device models, a model corresponding to the device indicated in the user input, determine a position, orientation and scaling of the computer-generated device model indicated in the user input based on the first image data; and output, to one or more image display devices, the first image data and the computer-generated device model overlaid over the image frame at the determined position, orientation and scaling.

In some examples, the device may be a mitral valve clip, and the computer-generated device model of the device may be a three-dimensional CAD drawing.

In some examples, the instructions may be configured to cause the one or more processors to determine a recommended location for transeptal crossing by a needle, generate a recommendation reference marker indicating the recommended location for transeptal crossing, output, to one or more image display devices, the first image data and the recommendation reference marker overlaid over the image frame at the recommended location, receive, from the first imaging device, subsequent image data of the target heart valve, determine a distal tip trajectory of the needle from the subsequent image data, determine a difference between a direction of the recommendation reference marker and the distal tip trajectory, and set a color of the recommendation reference marker based on the determined difference.

In some examples, the instructions may be configured to cause the one or more processors to receive a puncture device user input indicating a puncture device, determine, based on prestored puncture height data, a recommended puncture height for the puncture device indicated by the puncture device user input, generate a puncture reference marker indicating the recommended puncture height based on the prestored puncture height data, and output, to one or more image display devices, the first image data and the puncture reference marker overlaid over the image frame at a location of the recommended puncture.

Another aspect of the disclosure is directed to a system including an apparatus as described in any of the embodiments herein, and a second imaging device. The instructions may be configured to cause the one or more processors to receive, from the second imaging device, second image data of a plurality of image frames of the target heart valve, co-register the first image data with the second image data, and output, to one or more image display devices, at least portions of the first image data and the second image data overlaid on one another in a composite image.

In some examples, the one or more image display devices may include a first display image device and a second image display device, and the instructions may be configured to cause the one or more processors to output, to the first image display device, the first image data including one or more reference markers generated from the first image data, and output, to the second image display device, the second image data and the one or more reference markers generated from the first image data overlaid on the second image data.

In some examples, the first imaging device may be an echocardiography device, and the second imaging device may be one of a fluoroscopy device, a contrast-flow MRI device, or a CT device.

DETAILED DESCRIPTION

Figure 1:
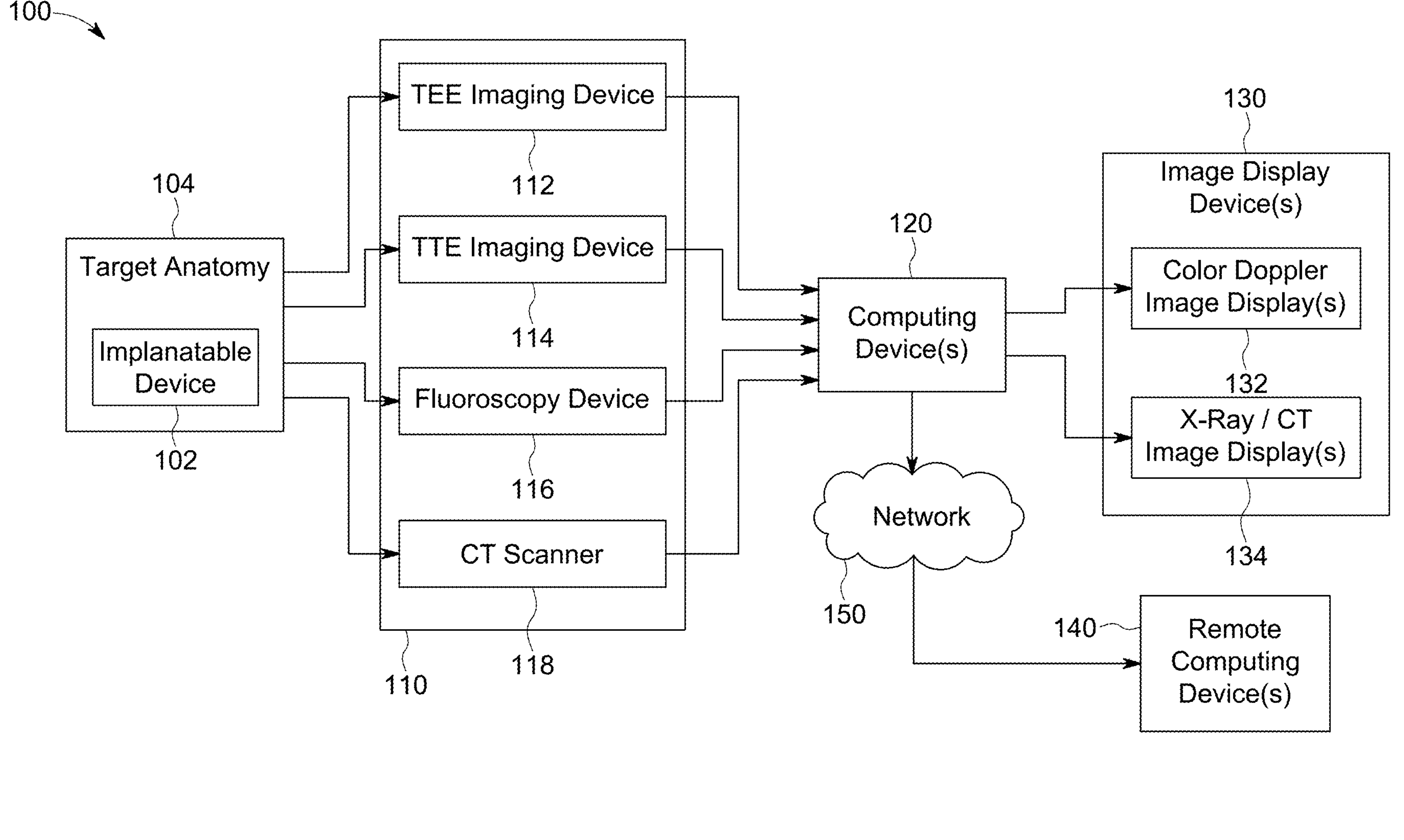
FIG. 1 illustrates a system in accordance with an aspect of the disclosure.

FIG. 1 illustrates a system 100 according to the present disclosure. The system 100 includes an implantable device 102 such as a valve repair implant. Examples of valve repair implants include the MitraClip™ and TriClip™ clips, made by Abbott Laboratories, for attachment to valve leaflets in order to reduce or minimize valve regurgitation through those leaflets.

The system 100 may further include one or more imaging devices 110, including but not limited to a trans-esophageal echocardiography device 112, transthoracic echocardiography device 114, a fluoroscopy device 116, a computerized tomography (CT) scanner, and so on. The imaging devices 110 may be directed toward the implantable device 102 or a target anatomy 104 of the implantable device 102. Sonography and echocardiology generally provide a 2D planar image of the section of the heart relative to the direction of an ultrasound transducer directed toward the patient, and the 2D images are typically presented in monochrome. Motion of the heart may be observed by video or still images using the 2D imaging technologies. Echocardiography may also provide visuals of 3D topographic surfaces of the heart anatomy and structures. Simultaneous visualization of two imaging planes (commonly referred to as X-plane or bi-plane), which are generally orthogonal planes, may be performed for procedures such as TMVr and TTVr.

The system may further include one or more computing devices 120 and image display devices 130. The imaging devices 110 may be connected to a computing devices 120, and may be configured to transmit imaging data to the computer devices 120 for processing. The computing devices 120 are connected to the image display devices 130, including but not limited to color Doppler image display devices 132, X-ray or CT image display devices 134, and so on, in order to provide a stream of image frames or video frames of the imaged target area. The displayed imagery may show flow over a duration of multiple cardiac cycles. The computing devices may further be connected to one or more remote computing devices 140 through a network 150.

Figure 2:
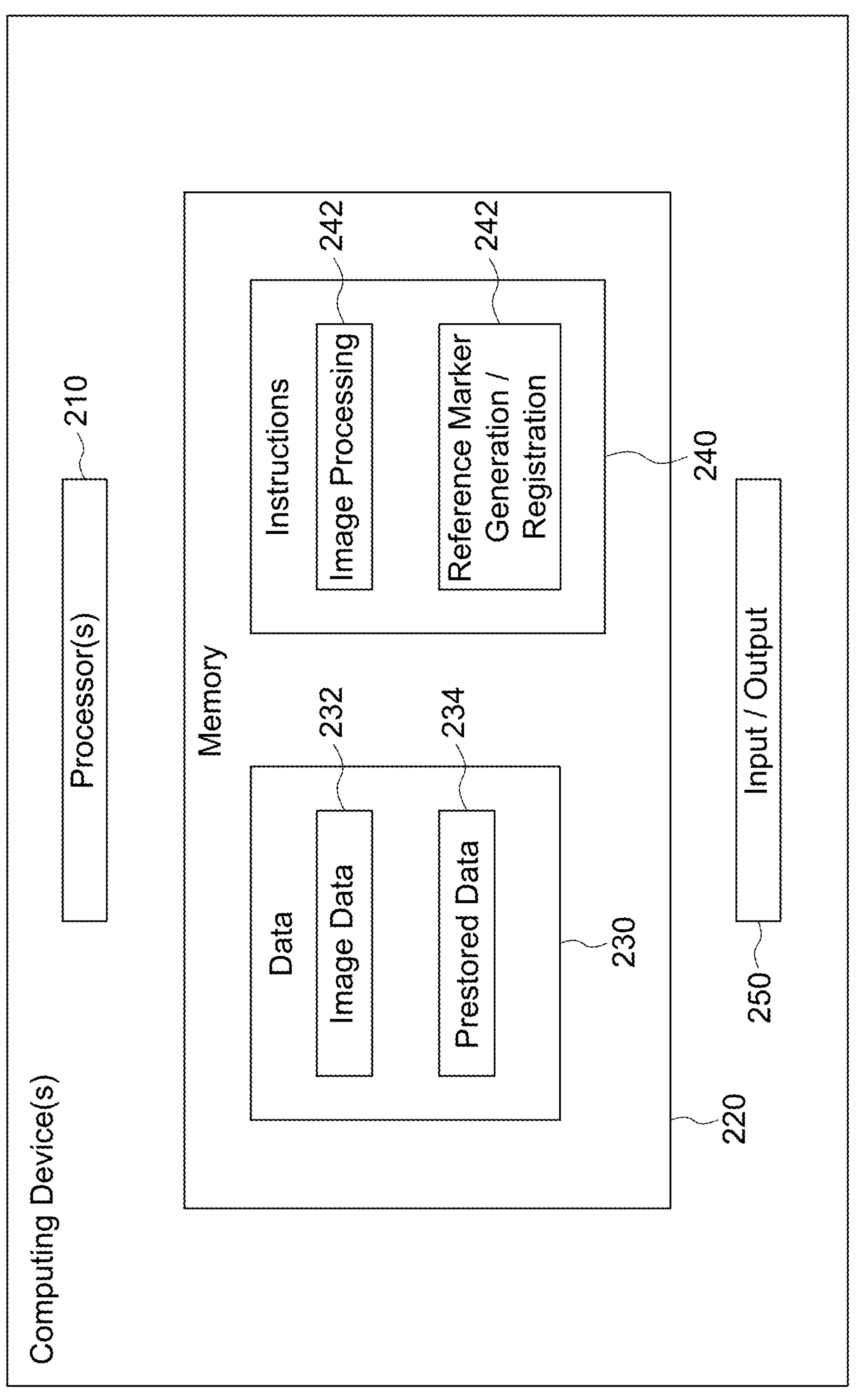
FIG. 2 illustrates a block diagram of an example computing device of FIG. 1.

FIG. 2 is a block diagram of the one or more computing devices 120. The computing devices 120 may include each of a processor 210, memory 220, and input/output connections 250 for communication with the imaging devices 110 and image output devices 130.

The processor 210 may be a well-known processor or other lesser-known types of processors. Alternatively, the processor 210 can be a dedicated controller such as an ASIC. The memory 220 can store information accessible by the processor 210, including data 230 that can be retrieved, manipulated or stored by the processor 210, in accordance with instructions 240 stored in the memory. The memory 220 may be a type of non-transitory computer readable medium capable of storing information accessible by the processor 210, such as a hard-drive, solid state drive, tape drive, optical storage, memory card, ROM, RAM, DVD, CD-ROM, write-capable, and read-only memories.

Although the system described herein is not limited by a particular data structure, the data 220 may be stored in computer registers, in a data store as a structure having a plurality of different fields and records, or documents, or buffers. The data 220 may also be formatted in a computer-readable format such as, but not limited to, binary values, ASCII or Unicode. Moreover, the data 220 can include information sufficient to identify relevant information, such as numbers, descriptive text, proprietary codes, pointers, references to data stored in other memories, including other network locations, or information that is used by a function to calculate relevant data. The instructions 230 may be a set of instructions executed directly, such as machine code, or indirectly, such as scripts, by the processor 210. In this regard, the terms "instructions," "steps," "programs" and "routines" can be used interchangeably herein.

Although FIG. 2 functionally illustrates the processor 210 and memory 220 as being within a single block, the processor 210 and memory 220 may actually include multiple processors and memories that may or may not be stored within the same physical housing. For example, some of the data 230 and instructions 240 may be stored on a removable storage device such as a CD-ROM. Also, some or all of the instructions and data can be stored remote from the processor 210, but may be accessed remotely, such as over the network 150. Additionally, the processor 210 can actually include a collection of processors, which may local or distributed resources such as on a cloud platform, and which may or may not operate in parallel.

The data 230 may include image data 232 received from the imaging devices and representing image frames stored for processing at the computing devices. The data 230 may further include prestored data 234, such as predetermined values and objects. Example of prestored and predetermined data are described in greater detail within the embodiments described herein. The instructions 240 may include one or more routines or algorithms to be executed by the processor 210. Examples of stored routines include various image processing routines 242 and reference marker generation and/or registration routines 244 as described herein.

Figure 3:
FIG. 3 illustrates a flow diagram of an example routine in accordance with an aspect of the disclosure.
Figure 3:
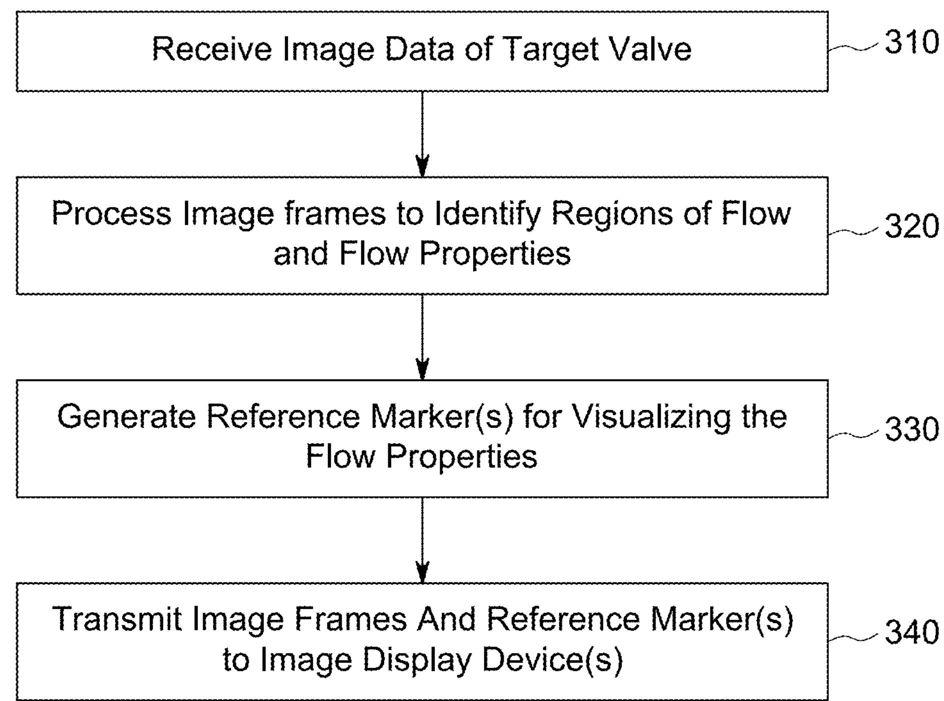

FIG. 3 is a flow diagram of an example routine 300 for generating a simplified regurgitation visual. At block 310, the one or more processors receive image data of the target valve, the image data may include several frames of images over a duration of time including multiple cardiac cycles.

At block 320, the one or more processors process the image frames in order to identify regions of flow and to determine properties of the flow regions, such as a direction and magnitude of the flow. The regions of flow may be identified using doppler-based imaging, such as Doppler echocardiography, and the direction and magnitude of the identified region of flow may be assessed using algorithms stored in the memory of the one or more computer devices. In some cases, Doppler echocardiography may be received from multiple image devices, such as TEE and TTE devices. In such a case, the TEE and TTE data may be co-registered in order to improve image quality.

Figure 4:
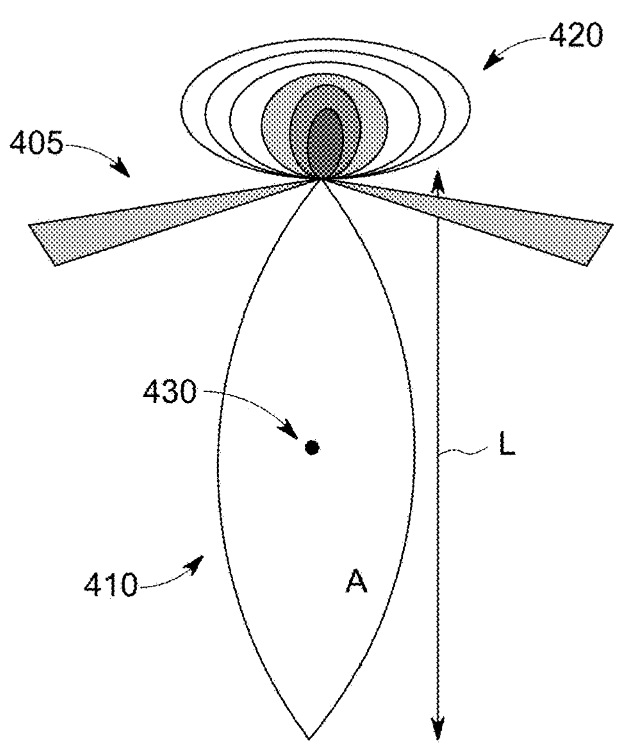
FIG. 4 illustrates an example augmented echocardiograph image frame in accordance with an aspect of the disclosure.

FIG. 4 is a diagram illustrating an example region of flow that may identified from an echocardiograph image frame by the one or more processors. The illustration shows a valve 405, which in this example illustration is a mitral valve, although in other examples different valves could be analyzed using the same or similar principles. The illustration also shows a region of backflow through the valve 405 in the form or shape of a jet 410. Properties of the jet include the jet length (L) and an overall area (A) of the jet 410. The illustration also shows a flow convergence region 420 on an opposite of the valve 405 from the jet 410 and indication a flow of blood towards the valve 405.

The flow data shown in the illustration of FIG. 4 may be used to determine properties of the regurgitation such as magnitude and direction.

With regard to magnitude, this may be derived from either one of the jet 410, the flow convergence region 420 or both.

Typically, a greater amount of flow results in a larger jet, indicating a greater amount of regurgitation. This means a size of the jet 410 is typically correlated to the magnitude of flow. Additionally, the flow convergence region 420 indicates the presence of increased flow of blood, in this case back towards the valve 405. The size of the flow convergence region 420 is typically indicative of a size of the opening in the valve 405 causing the regurgitation. Thus, the area of the flow convergence region 420 generally corresponds to the magnitude of the flow.

Multiple tools may be used to determine the magnitude of the regurgitation from the echocardiograph imaging. For example, position, intensity and shape analysis (PISA) may be combined with other cardiac parameters, such as pulmonary vein measurements, pressure half-time (PHT) calculations, mean diastolic gradient calculations, etc., in order to improve determination of the regurgitation magnitude.

With regard to direction of the regurgitation, this can be inferred by analysis of the jet 410. For instance, a central point 430 of the jet may be determined, such that a line from the valve 405 to the central point 430 may indicate an overall or average direction of the regurgitation. Determining the central point 430 may involve determine a point for which equal area of the jet is on either side of the point. Alternatively, the central point 430 may be weighted, whereby flow at different points of the jet 410 may be assessed in order to determine a point for which equal amounts of blood flow are on either side of the point.

The flow data can also be used to determine a location, range or width, of the regurgitation, and direction and magnitude of the regurgitant jet. Range may be determined from any one or combination of a jet width (W), a width of the flow convergence region 420, or the jet area (A). The determination may utilize mathematical models and/or statistical models including but not limited to machine learning models or artificial intelligence programs. Generally, wider regurgitation may indicate a wider opening during systole coaptation of leaflets in the valve that is causing the regurgitation. The flow data may further be used to determine a number of separate regurgitations. For instance, when the flow data indicates two distinct jets with a non-regurgitant or relatively less regurgitant region in between, the flow data of each separate regurgitation may be separately computed and tracked. Additionally or alternatively, in cases of data indicating separate jets, the flow data may still be treated as a single jet by summing the data.

Returning to FIG. 3, at block 330, the one or more processors generate one or more reference marks for visualizing the determined properties of the identified flow. For instance, an arrow may be generated. The arrow may have a direction corresponding to a direction of the regurgitant flow. Additionally, the arrow may have a second feature corresponding to a magnitude of the regurgitant flow, a third feature corresponding to a width of the regurgitant flow, or both. For instance, the second feature may be a length of the arrow, and the third feature may be a width or thickness of the arrow. Alternatively, a feature of the arrow may be its color, whereby a change in color may indicate an increase or decrease in any one of the above-noted properties. By combining these features into a single arrow, the one or more processors are capable of generating a single reference mark capable of indicating each of flow direction, magnitude and width.

Figure 5:
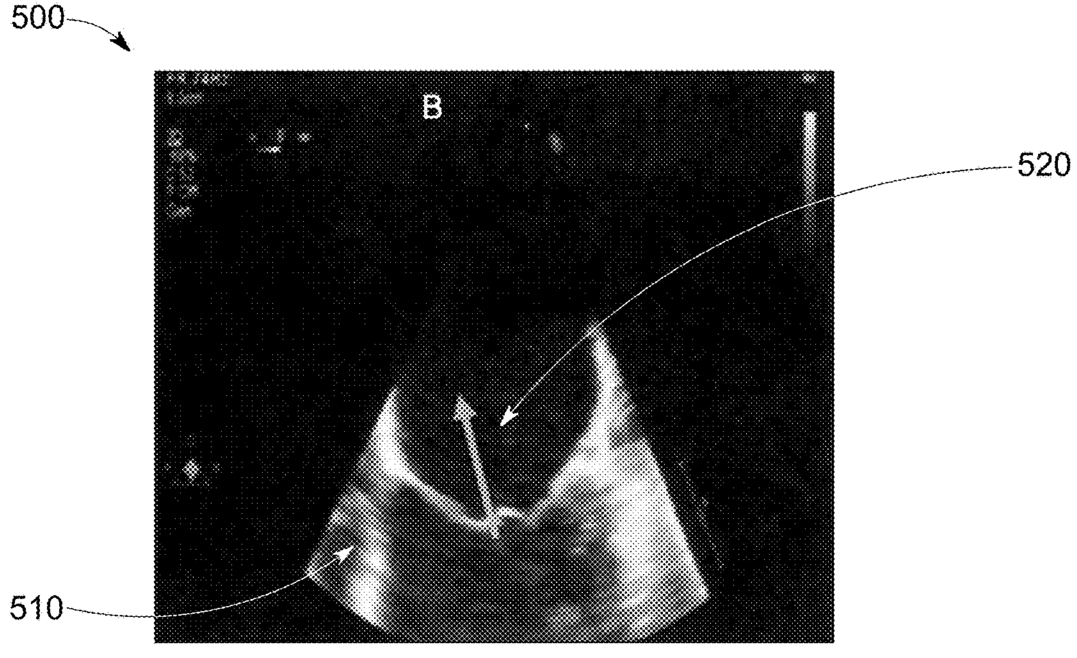
FIG. 5 illustrates an example composite image frame in accordance with an aspect of the disclosure.

At block 340, the one or more processors transmit the image frames and the reference mark to the one or more image display devices for display. The image frames and reference mark may be displayed on a common display, such as by overlay. An example overlay or composite image 500 is shown in FIG. 5. The image 500 includes each of echocardiograph details 510 and a reference mark arrow 520. The arrow 520 includes each of a direction, a length and a width in order to characterize the regurgitant flow shown in the image.

As can be seen from FIG. 5, determining regurgitant flow from echocardiography without the arrow is especially difficult, given the faint and grainy appearance of flow within the image. While color Doppler imaging can provide some amount of improvement to the representation of regurgitant flow, the spectrum of colors representing speed of flow and the amorphous graphical depiction of regurgitation make deciphering the imagery more complicated. By contrast, the arrow 520 is clear to see and easy to interpret. Thus, an operator relying on the composite image of FIG. 5 would readily and easily be able to process the presence, magnitude, direction and width of the regurgitant flow at the target valve. The arrow is capable of being superimposed in any type of display, including but not limited to 2D echo displays and 3D echo display.

Figure 6:
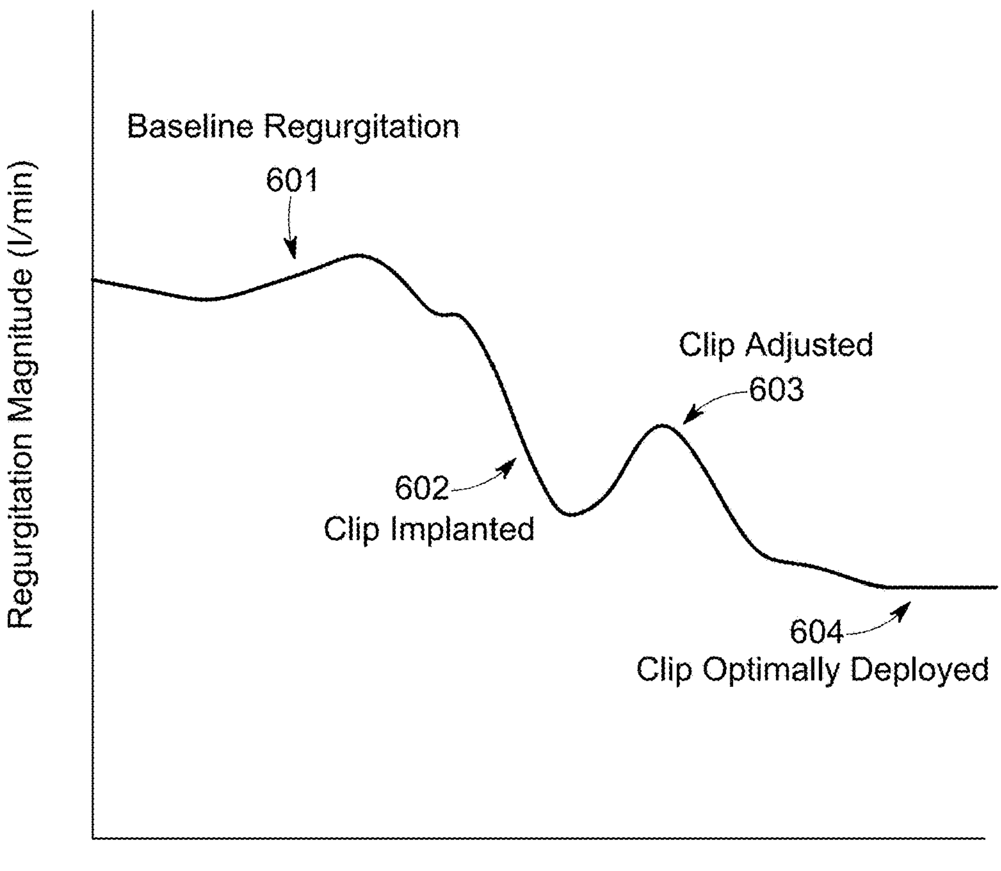
FIG. 6 is a graph of regurgitation magnitude plotted against time during a coaptation clip implantation procedure.

Greater and clearer knowledge of the defect further allows for more informed repair, such as correct placement of leaflet clips in order to mitigate or minimize the regurgitation. The improved feedback also allows for more efficient repair with fewer implants. For instance, FIG. 6 is a graph illustrating an example change in regurgitation as a clip is deployed. At a beginning of the procedure (601), regurgitation magnitude is at a baseline level, which is relatively high, and more specifically higher than an optimal level. Subsequently (602), the clip is implanted and regurgitation magnitude drops to a lower level but not as low as the optimal level. Next (603), in order to reduce regurgitation further, the clip is adjusted on the leaflet. If it can be clearly and readily seen from the change in the length of the arrow on the display that the regurgitation has increased, then it can be determined relatively quickly that the clip adjustment was incorrect, and the clip can be adjusted in a different manner to counter the increased regurgitation. Finally (604), subsequent adjustments of the clip results in the clip approaching or reaching an optimal deployment, with regurgitation magnitude decreased to a minimum during the procedure. The use of composite echocardiography and overlaid arrows makes it possible to quickly and confidently determine that the regurgitation magnitude is actually decreased or minimized.

The example of FIG. 5 shows an example marker for two-dimensional echo imaging. However, other types of markers may be more useful or informative depending on the type of imaging being performed. For instance, if the display supports three-dimensional echo imaging, a circular marker may be used instead. For instance, a center of the circle may indicate a center of the regurgitation flow, which may correspond to a location from which the regurgitation occurs, and a radius of the circle may indicate a range or width of the regurgitation. The circle marker may be overlaid in addition to or in place of the arrow marker.

The example of FIG. 5 also shows a single marker. However, in other cases, multiple jets may be present. In such cases, multiple markers may be generated and overlaid on the display. The presence of multiple jets may be determined by comparing flow rates in the processed image, such as if there is a flow rate below a minimum threshold at a first point and a flow rate above a maximum threshold at two other points on either side of the first point.

Multiple markers may be provided in other cases as well, such as presenting present and historical markers on screen for the sake of comparison. For instance, and returning to the example of FIG. 6, after placing the clip at step (602), the arrow marker can be stored in the memory of the one or more computing devices for later access. Then, at either steps (603) or (604), the stored marker can be accessed from memory and overlaid with the marker of a later step to compare whether regurgitation has improved or worsened.

The example of FIG. 5 also shows only a single marker illustrating the regurgitant flow during a single image frame. However, since multiple image frames are captured and processed by the one or more computing devices, it is also possible for reference markers to be determined, generated and graphically represented based on a combination of current and past images. For example, an autocorrelated mean frequency may be computed using input data from the imaging devices. The input data may represent flow, and may allow for comparing the phase of the Doppler signal in previous input data with the phase in the input data. In other instances, autocorrelation may be computed from each point of a stream of image frames by comparing the phase of the Doppler signal on each line of one frame with the phase on the previous image. The resulting autocorrelated flow data may be used to generate an arrow reference marker that may represent any one or combination of point of origin, direction of the regurgitant jet, velocity and flow. Alternatively, a vector indicating regurgitant flow may be determined for each individual frame and a running average of properties of the vector may be tracked in order to generate the arrow reference marker based on the series of image frames. Autocorrelated or running average results may be steadier over time than reference markers based on instantaneous data, since the flow is typically not steady over the course of a cardiac cycle or even from cycle to cycle. As such, a reference marker generated from cumulative results may become steadier over time as more data is processed an incorporated into the cumulative result. The steadier reference markers can be helpful for making the regurgitation faster and easier to interpret from the display.

The reference markers can be presented on the display in lieu of or in addition to other visuals for interpreting regurgitation. For example, color Doppler is commonly used to display regurgitant flow data. The one or more processors may be capable of displaying either the reference marker on an echocardiograph without the color Doppler, the color Doppler without the reference marker, or overlay both on the same image frame or stream of image frames. Control of the type of visual data being displayed could be based on a user input, such as one or more switches, to control a mode of display. Modes of display may include color Doppler only, reference marker only, or combined Color Doppler and reference marker. Furthermore, reference markers may be toggled on or off to be used as a more efficient assessment of the procedural echocardiography.

Additionally or alternatively, other reference markers and visuals may be included in the imaging output on the display. For instance, the one or more processors may be configured to identify features or landmarks within the image frame, generate labels for the identified details and overlay the labels on the analyzed image frame. Such features and landmarks may include, but are not limited to, the implantable device or other devices for implantation or repair, valve commissures, multi-point annulus/valve plane, direction of flow, transeptal crossing, etc. The identified details may further be registered with the image frame so that the labels can be moved around and properly overlaid on future image frames.

Determining the landmarks and features may be performed automatically according to a routine programmed at the one or more computer devices. In some examples, the routine may be a machine learning algorithm. Example machine learning algorithms that may be utilized include but are not limited to vector machines, artificial neural networks such as a convolutional neural network (CNN) or recurrent neural network (RNN), stochastic approaches such is logistic regression, a Naïve Bayes algorithm, etc.

For landmarks and features identifying regurgitant flow, the machine learning algorithm could be trained using flow/imaging data pairs obtained from past procedures or from a simulator generating flow and image data. In such a simulator, pressure wires, flow sensors or both could be used to obtain the flow data, and the clips could be placed in both optimal and sub-optimal positions in order to obtain useful training data. The trained algorithm could be used to analyze image/flow data pairs received during subsequent procedures, such as TEE imaging data sets and corresponding flow measurements obtained through doppler imaging. The paired data may relate forward pressure gradient, regurgitant jet size or both to corresponding video or image frames at one or more cardiac phases, such as peak systole (e.g., to evaluate regurgitant flow) or mid- or late-diastole (e.g., to evaluate mitral gradient). Data set differences may be computed between pre-Clip and post-Clip states, between post-Clip at discharge TEE or TTE images and post-Clip at 30 days TTE images, or both.

Alternatively, the landmarks and features may be initially identified manually, and subsequently tracked in future image frames by registration.

Figure 7A:
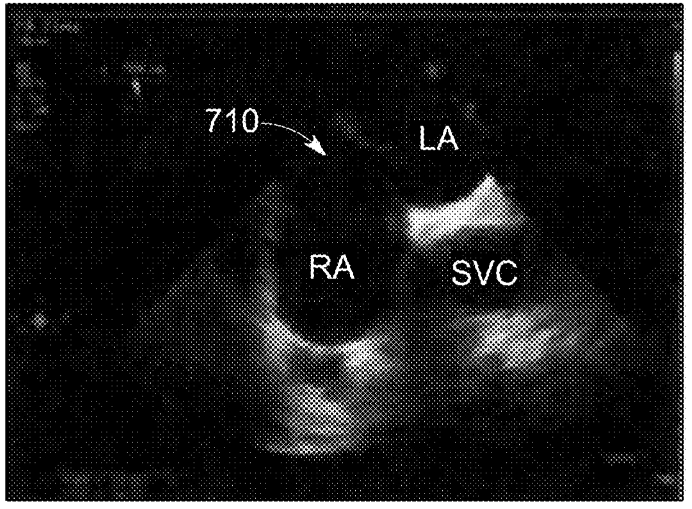
FIGS. 7A-7C are example labeled image frames in accordance with an aspect of the disclosure.
Figure 7B:
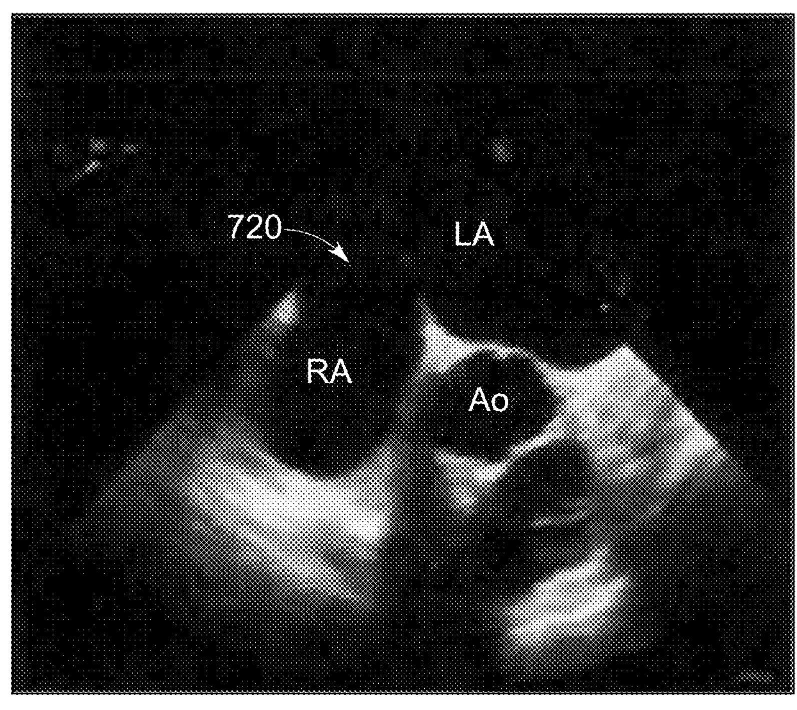
Figure 7C:
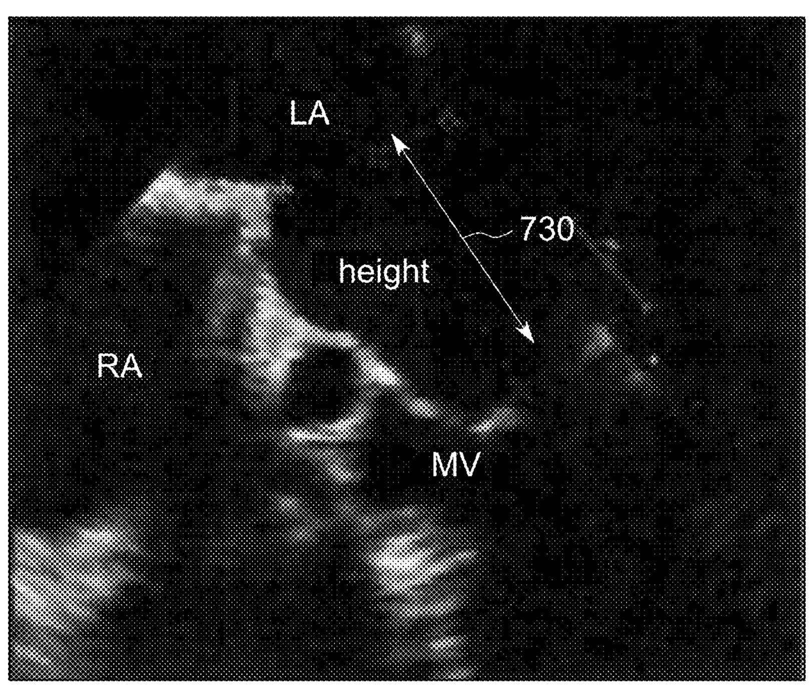

FIGS. 7A-C illustrate example image frames including labels and markers.

In the example of FIG. 7A, a TEE view is shown with each of the left atrium (LA), right atrium (RA) and superior vena cava (SVC) having been labeled. Additionally, a reference marker arrow 710 is included to illustrate the transeptal crossing, which otherwise may not be easily visible from the TEE view. The transeptal crossing may be determined based on image data from the same or another imaging device pointed from a different angle or view, such as from a bicaval view.

In the example of FIG. 7B, a TEE view is shown with each of the left atrium (LA), right atrium (RA) and aortic root (Ao) having been labeled. Additionally, a reference marker arrow 720 is included to illustrate the transeptal crossing, which otherwise may not be easily visible from the TEE view. The transeptal crossing may be determined based on image data from the same or another imaging device pointed from a different angle or view, such as from a short-axis base (SAX-B) view.

In the example of FIG. 7C, a TEE view is shown with each of the left atrium (LA), right atrium (RA) and mitral valve (MV) having been labeled. Additionally, a reference marker 730 and label are included to illustrate a measurement of distance ("height") from the transeptal crossing to the valve, which otherwise may not be easily discernable from the TEE view. The height may be more clearly seen and determined from image data from the same or another imaging device pointed from a different angle or view, such as from a four-chamber view. Changes to image angles may be performed manually or according to an algorithm.

Positions of the reference markers and labels may be determined by averaging or autocorrelation in order to avoid jitter at the display. Additionally or alternatively, the markers and labels may be registered so that the selected position on the display changes along with changes to the image. For example, as anatomical features or landmarks are identified in the image, the identification of these features may be used to determine an optimal view. Example anatomical features may include commissures, septal wall, and the valvular plan. Anatomical features and landmarks may be identified and labeled using a machine learning algorithm such as any of the example algorithms described herein. For instance, the machine learning algorithm may be trained on parametric dataset collections or summarized datasets from a large population of patients. Examples of parameters of such a dataset collection includes but is not restricted to: atrial and ventricular length and width; valve annular dimensions (e.g. medial/later and anterior/posterior); anterior leaflet and posterior leaflet lengths; location commissures, regions of the anterior and posterior leaflets (e.g., A1/P1, A2/P2, A3/P3); other information about valve anatomy, information about blood flow patterns; device orientation, etc. Additionally or alternatively, the location of a patient's regurgitant jet could first be determined and then represented relative to these cardiac dataset landmarks—and can be compared to the broader patient population dataset.

Identified landmarks and anatomical features may be further used in order to determine additional controls, including but not limited to suggested viewing angles. For instance, a viewing angle from the X-plane could further be automatically centered by the one or more processors according to an algorithm or machine learning algorithm such as any of the example algorithms described herein. In such an instance, the one or more processors could determine a suggested orientation for viewing the clip in order to improve understanding of the clip grasping. The suggested orientation could be based at least in part on the previously identified anatomical features or landmarks.

One or more TEE imaging strategies may involve sweeping through the entire valve from different orientations. For instance, a first sweep may be conducted from a 0° orientation from lateral to medial positions through the esophagus. A second sweep may be conducted from an inter-commissural view between medial and lateral commissures of the mitral valve, whereby the probe is rotated to move between anterior and posterior leaflets and find a maximum width between the leaflets. The sweep may be a bi-plane sweep and may further be useful for visualizing a regurgitant jet within the view of the left ventricular outflow tract (LVOT). A third sweep may be conducted from a long-axis view, whereby the probe is rotated from lateral to medial positions. The long-axis view may be useful for viewing clip grasp angles and identifying calcification in the grasp angle. The imaging may be performed using 2D. 3D imaging, such as a 3D en face view, may further enhance understanding and visualization from the 2D imaging.

In some instances, the viewing angle may be chosen in order to improve identification of anatomic features in the images. One approach for determining a view for obtaining anatomic features may involve acquiring a range of 2D and/or 3D X-plane echocardiography data and rotating the measurement plane either until leaflet lengths appear as having a maximum dimension, or until leaflet gaps appear as having a maximum, or to a point where commissure-to-commissure distances appear to have a maximum, or to a point where the angle between the septal wall and the valvular plane appears to have a maximum. Manipulations to these viewing angles help to measure true angles and lengths without foreshortening. For instance, accurate measurements of leaflet gaps and leaflet lengths are advantageous to anticipate clipability. For further instance, an accurate measurement of the septal wall to valve plane angle is are advantageous to guide trans-septal puncture.

Viewing angles may also be chosen based on a detected regurgitant jet. for instance, for an orientation advantageous for viewing the leaflets grasping, the view plane may be rotated or jittered so that a gap distance between leaflets is at its maximum at a same location as where a regurgitant jet is present. The same or similar view plane may be advantageous for accurately measuring leaflet length, which in turn may be a useful properties for judging clipability of the clips to the leaflets since the leaflets need to be long enough in order to be grasped by the clips successfully. If multiple regurgitant jets are present, each regurgitant jet may be associated with a respective grasp location, and views of the respective grasp locations may be independently determined. One grasping location could be selected and viewed. After a clip is placed at the selected grasping location, the behavior of the valve and the pattern of regurgitant flow could change, so the viewing angle could be updated based on the changes in the regurgitant jet in order to provide better viewing for further adjustments.

Aside from the markers to visualize the anatomical features, images may be enhanced in order to aid with visualization of devices. For instance, features or an outline of a device or surrounding anatomy included in an image may be enhanced based on detection of the device or surrounding anatomy in another image frame, either using the same imaging device or a different imaging device. One example anatomical feature that may be detected from separate image frames is a leaflet edge. Typically, in the case of using echocardiography to implant a clip to the leaflet, the leaflet edge may be obscured within the echocardiograph image frames by the implanted clip, making it difficult to assess the implantation. In order to overcome this challenge, a line may be generated and overlaid over the leaflet edge in order to provide an improved visualization of the leaflet edge. In other instances, other reference markers such as tick, circles and other shapes may be used to indicate the same or similar anatomical or device features or outlines that would otherwise be difficult to see in the image.

Generating the reference markers over the anatomical or device features may be performed manually or automatically. In the case of manual generation, the one or more processors may be configured to receive a user input including an illustration to be made on the image frame. The one or more processors may further register the input so that it moves with the rest of the image target in future image frames.

In the case of automatic generation, the one or more processors may be configured to receive a user input initiating an automated leaflet edge detection program. The program may involve automatically obtaining an offset image that is outside of the current image plane by a predetermined offset distance. An offset image may be automatically obtained on both sides of the image plane. Since the implanted device is only present in the current image plane and is not present in the planes of offset images, features and outlines of the leaflet edges can be more easily detected in the offset images. In some instances, the one or more processors may further analyze the offset images to detect the leaflet edges. Once the leaflet edges have been detected in each of the offset images, the one or more processors may interpolate a position of the leaflet edges within the current image plane from the offset images. Finally, the one or more processors generate a reference marker at the determined interpolated position of the leaflet edges within the current image plane, and may output this reference marker to the display devices to be overlaid over the image frames. In this regard, the displayed image frames present a clear digitally generated mark of the leaflet edges for assessment of the clip implantation, without requiring one or more separate images to be consulted.

Acquisition of the offset images may be performed using a gated acquisition scheme in order to ensure that the interpolated images present the surrounding anatomy, particularly the leaflet edges, at a common phase of the cardiac cycle.

Figure 8A:
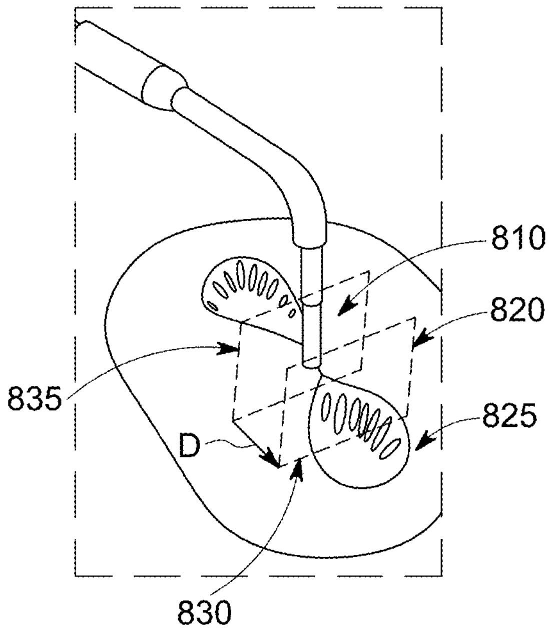
FIGS. 8A-8C are example image frames illustrating a leaflet edge interpolation routine in accordance with an aspect of the disclosure.
Figure 8B:
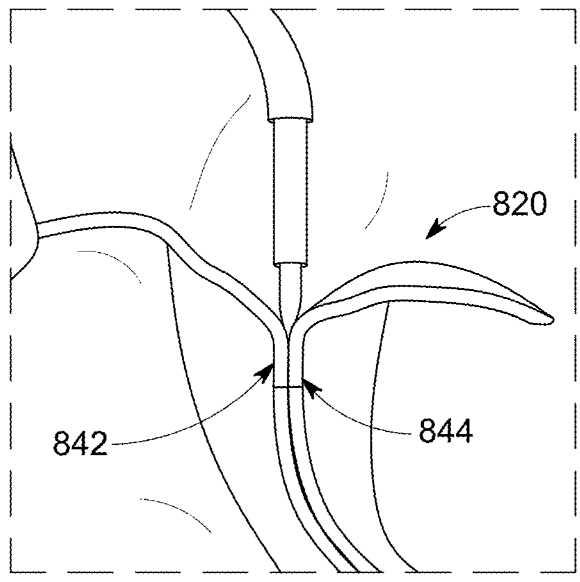
Figure 8C:
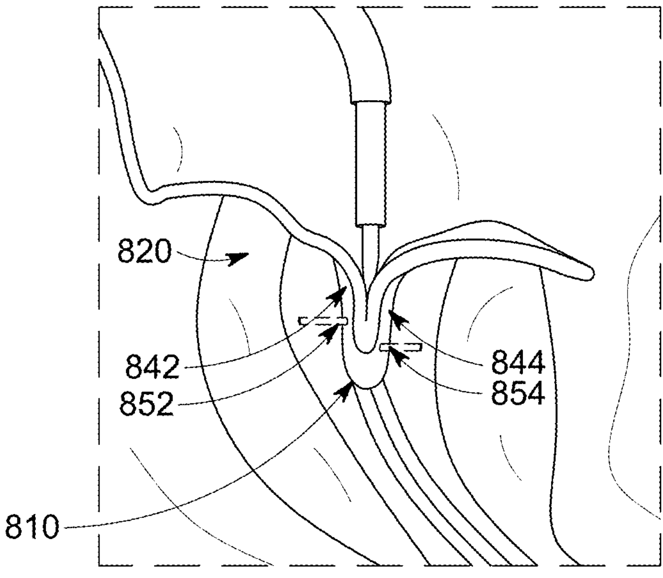

FIGS. 8A-8C illustrate the process of automatically generating a leaflet edge reference marker. FIG. 8A illustrates a perspective view of a clip 810 being implanted in a mitral valve 820. The clip attached to each leaflet 825 of the valve at a relatively central location. FIG. 8A also illustrates an offset plane 830 that is offset to one side of an image plane 835 in which the clip 810 is present. The offset distance D may be selected based on a width of the clip 810, whereby the offset plane 830 is just outside the space occupied by the clip 810.

FIG. 8B shows a cross-sectional view of the valve 820 along the offset plane 830. FIG. 8C shows a cross-sectional view of the valve 820 along the image plane 835 including the clip 810. As shown in FIG. 8B, the leaflet edges 842, 844 are not pressed together by the clip and can be clearly seen in the offset plane 830. By contrast, in FIG. 8C, the clip 810 presses the leaflet edges together, making it difficult to recognize the leaflet edges. Based on the positions of the leaflet edges in the offset plane 830 of FIG. 8B, the positions of the leaflet edges in the image plane of FIG. 8C can be interpolated, and reference markers 852, 854 can be generated and overlaid on top of the image plane in order to visualize the leaflet edges.

The portions of the leaflet edges detected in the offset plane may be manually detected and selected, or they may be automatically identified. In the case of automated detection, the leaflet edges may be detected using an algorithm or machine learning algorithm such as any of the example algorithms described herein. For instance, a predicate patient imaging dataset pool (typically echocardiographic or electro-magnetic sensing based) may be utilized and the machine learning algorithm may automatically compute leaflet edges based on information from the dataset pool. The computed leaflet edges may in turn be used to determine leaflet length interacting with the device.

Additionally or alternatively, leaflet edges can be determined according to contrast between image pixels having at least a predetermined amount of contrast. Leaflet lengths may further be estimated based on a length from the leaflet edge to a valve edge and according to fitted angles to segments of the leaflets. As discussed above, accurate measurement of leaflet length may involve adjusting the imaging plane until the length of leaflets appears to have a maximum in order to ensure that true length is being determined and to avoid interpreting foreshortened dimensions. Also, leaflet lengths can be monitored at multiple specific cardiac phases and averaged in order to provide an accurate measurement. For instance, the lengths may be measured during end-systole and during end-diastole, and then averaged. Additionally, taking measurements at multiple phases allows for measurements to be examined for discrepancies. For instance, if a difference in leaflet length between systole and diastole exceeds a predetermined threshold amount, the measurements may be disregarded and acquisition can be repeated with a different acquisition plane or a thicker imaging slice.

In some examples, the interpolation may be a straight or curved line based exclusively on the edges identified in the offset plane. In other examples, the interpolation may be aided or enhanced by external information, such as a predetermined valve model. The valve model may include structural information about valve morphology, whereby features in the offset plane may be identified and associated with corresponding features in the predetermined model. The morphology of a valve model may provide a more accurate representation of valve structural within the target anatomy. Furthermore, the correspondence between the predetermined model and the imaging data may rely on any one or combination of imaging tools, including but not limited to 2D images, 3D images, or 4D images. In situations where presence of a device within the image creates artifacts or causes signal drop out (e.g. due to a shadow in the echocardiography data), data from images of the same patient acquired prior to appearance of the artifact may be used to supplement the current images and to fill in missing information through interpolation.

Additionally, once the reference markers of the leaflet edges have been generated, the reference marker may be registered in place with the imaging data in order to adjust the leaflet edge in future image frames. The registration may be based on one or more imaging modalities of the imaging data. In some examples, the registration may further be based on the predetermined valve model.

The capture of images within the offset plane may be performed automatically instead of requiring manual manipulation of the echocardiography probe. Automatic imaging adjustments may include changes to one or both of the angulation or the offset of the plane away from the implant center at the image plane.

Figure 9A:
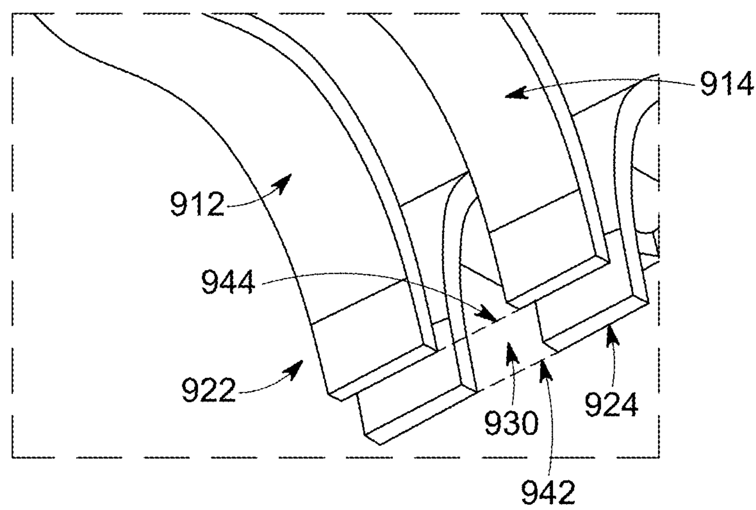
FIG. 9A is an illustration of another a leaflet edge interpolation routine in accordance with an aspect of the disclosure.
Figure 9B:
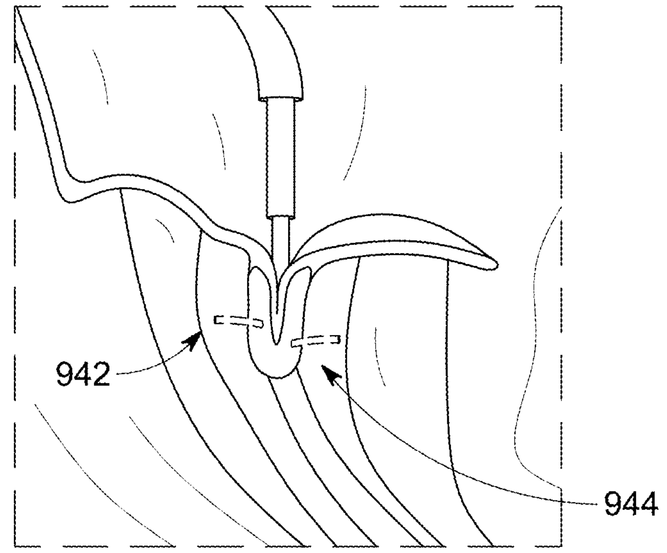
FIG. 9B is an example image frame from the illustration of FIG. 9A.

The example of FIGS. 8A-8C demonstrates interpolation using a single offset image. As mentioned herein, in some instances, offset images may be obtained on both sides of an image plane and used to device the interpolated leaflet edge position in other frames in order to provide more accurate estimates of leaflet edge position in the image plane. For example FIGS. 9A and 9B illustrate imaging of leaflets on either side of the clip using two offset sections. In FIG. 9A, section views of the leaflets 912, 914 are collected on each of a first side 922 and a second side 924 of a clip plane 930. Data from the section views may then be processed in order to interpolate a continuous leaflet edge 942, 944 for each of the imaged leaflets 912, 914, thereby connecting the imaged edges from each of the first side 922 and second side 924. In FIG. 9B, the interpolated edges 942, 944 are superimposed over the leaflets 922, 924 within a cross-sectional image obtained in the clip plane 930. The imagery in FIG. 9B allows for fast and intuitive understanding of the clip placement so that it may be readily recognized when adjustments are needed and in which direction to adjust.

Other programs may enhance the image using data external to the image data. For instance, the one or more processors may include a program for detecting a device in image frame data and overlaying a computer-generated model of the detected device in the display. The computer-generated model may be stored in memory of the one or more computing devices, such as a computer-aided drafting (CAD) model included in a CAD library. A device-type input may be provided to the one or more processors indicating a type of device present in the image frame. Then, the one or more processors may access correlation data associated with the type of device indicated in the device-type input, the correlation data being previously obtained based on known images of the selected type of device. The correlation data may be stored in the memory of the one or more computing devices. Using the correlation data, the one or more processors may determine a location and correction orientation/scaling of the device within the image frame. In one example, a least squares technique may be used to perform registration between the computer-generated model and the image frame. Once the position, orientation and scaling of the device in the image frame has been determined, the one or more processors can output the image frame data with the computer-generated model overlaid in the correct place, and at the correct orientation and scale.

One example application of a program to visualize devices is detection and visualization of a MitraClip™ implant within an echocardiograph. The program may begin by receiving an input indicating the MitraClip™, and then accessing from memory correlation data regarding a shape of the MitraClip™ and a three-dimensional CAD drawing of the MitraClip™. The echocardiograph image frame may then be analyzed according to the correlation data to detect a position, orientation and size of the Clip, and finally, the CAD drawing may be aligned with the detected features in the echocardiograph in order to provide a proper overlay of the CAD drawing over the image frame. As image frames are fed to the processor and then to the display, the CAD drawing may be rotated and reoriented based on detected motions in the received echocardiograph data.

In some examples, the one or more processors may be further programed to remove a selected device from display. For instance, instead of overlaying the detected artifacts of a device present in the image frame, the one or more processors may be programmed to negate the detected image artifacts, thus making visualization of other image details, such as surrounding anatomy of the device, easier to interpret on the display. Continuing with the example of the MitraClip™, the program may be a CAD model subtraction capable of obscuring the clip implant and its image artifact so that the leaflets to which the clip is implanted on can be more clearly seen on the display. Such an application may be useful for assessing implantation of the clip, such as estimating leaflet insertion in the clip. Thus, if there is a problem of the clip failing to grasp the leaflet or slipping off its target either during or after the procedure, this problem can be easily detected in the displayed image frames.

In the above examples, the labels and reference markers visualize present features. However, in other examples, labels and markers may be used to provide recommendations on the display. For instance, prior to transeptal crossing with the needle, an arrow may be generated and displayed to visualize a recommended or ideal location for transeptal crossing, a recommended or ideal angle for the transeptal crossing, or both.

Additional recommendations may be determined and provided on screen. For example, if a recommended needle position or angle is provided on screen, a position or angle of the needle may be detected in a future image frame and compared to the recommendation. Then, a color of the recommendation marker may change depending on a difference between the detected feature and the recommended feature. For instance, a current distal tip trajectory may be compared to a target vector, and a difference in magnitude between the two may be determined. The determined difference in magnitude may be classified according to preset data, and a color of the displayed recommendation may be selected according to the classification of the determined difference in magnitude.

In some examples, the recommendations may be determined by a machine learning algorithm such as any of the example algorithms described herein. The algorithm may be trained on data from a broader patient population dataset, such as data collected during prior therapeutic procedures. This may include data showing changes to or elimination of regurgitation associated with other features such as clip placement. Other data pairs that may be used for training data may include but is not restricted to: trans-septal puncture height paired with procedure time; trans-septal puncture height paired with procedural success rate; or trans-septal puncture height paired with valve regurgitation reduction. Evaluating data captured during a subsequent procedure using the algorithm may result in an output of suggested changes to be carried out during the subsequent procedure.

For example, a recommendation location for transeptal crossing may be determined automatically after providing an input of the delivery system being used. Parameters of the optimal septal crossing specific to the delivery system (e.g., distal curve, distal straight length to implant tip relative to the septal crossing point, annular plane relative to the septal crossing point, leaflet lengths relative to the annular plant) may be accessed by the algorithm to ensure that the recommendation location is an adequate height above the valve and allows for advancing the implant below the leaflets to enable grasping. Other parameters utilized by the algorithm may be measured in the annular plane. Transeptal height may be measured using the TEE four-chamber view. Leaflet lengths may be determined according to the algorithms described herein. An output of the algorithm may be an implant height above the valve corresponding to the recommended location for transeptal crossing.

For further example, a recommended puncture height location may be shown by use of an arrow, line, or shaded region on the display. Recommendations may be based on an input of a particular type of device being inserted, whereby the input may be received manually. The particular type of device may inform the recommendation. For instance, if a MitraClip™ device is being inserted, a puncture height location of about 3.5-4 cm from the mitral valve plane may be recommended since this height allows for proper clip steering and positioning. In other instances, shorter puncture heights may be preferable, or a more anterior puncture may be preferable, such as in the case of ablation catheters, left-atrial appendage occlusion devices, or transcatheter annuloplasty devices.

These labels and reference markers allow for information to be conveyed in the image display in a simplified fashion, and through relatively simple forms of image rendering. This, in turn, allows for more efficient streaming of the produced image frames, so that the image frames can be efficiently streamed from a remote location without latency issues. The ability to stream the image frames at a remote location opens up additional opportunities that would otherwise not have been available with more complex imaging and image rendering techniques.

One example ability is to incorporate features of the echocardiography image frames into fluoroscopy image frames or vice versa. The one or more processors may co-register the echocardiography and fluoroscopy images, detect objects in one or both of the images, and determine a position of the detected objects in the other of the images based on the co-registration. Typically, information appearing in echocardiography image frames would be difficult to reproduce or represent in a fluoroscopy image. For instance, information conveyed by color Doppler would require all color doppler data to be displayed with the fluoroscopy image. By contrast, replacing the color Doppler information with a reference marker allows for easier incorporation of this information with the fluoroscopy image. Similarly, the simplicity of the reference marker makes it easier to process and interpret additional information on the display of the echocardiography image frames. This allows for details captured in the fluoroscopy images to be overlaid or included in the echocardiography images without sacrificing clarity of the images. In one such example, an implanted clip that is more visible in the fluoroscopy images than echocardiography images may be isolated in the fluoroscopy image data and the isolated structure may be superimposed on the cardiography display. Such a feature may be toggled on and off by user input, such as by viewing the implanted clip during leaflet grasping to ensure that the clip grasps properly at an appropriate angle. In other examples, data may be isolated and extracted from other imaging modalities, including but not limited to intracardiac echocardiography (ICE), contrast-flow MM, CT, and so on. The incorporation procedure can be applied to different modalities whether they are synchronous or asynchronous. In the case of asynchronous imaging modalities, in which one imaging technique may interfere with the other, interleaving may be performed to collect interleaved image data for the composite image.

Another example ability is to share image data between multiple locations while the implantation procedure is occurring. While streaming full color Doppler images and the like may not be possible due to bandwidth and latency issues, abbreviated image data could be transmitted efficiently and speedily over a network connection to a remote computer device. This may allow experienced clinical specialists at a remote location to observe the image data being displayed at the procedure and to communicate helpful insights or recommendation as the procedure is underway. Such a remote proctoring setup could allow clinical specialists to observe and attend more procedures than currently possible, and to provide feedback during each of those procedures.

Generally, the above-described image processing and augmentation techniques may further be enhanced by the use of gated acquisition, in which the system further includes a cardiac sensor and the one or more processors are configured to determine a phase of the cardiac cycle from data received from the cardiac sensor. The one or more processors may further be configured to obtain image data at a given phase of the cardiac cycle, or to output image data limited to a given phase of the cardiac cycle. For instance, in the case of assessing mitral valve regurgitation, a given phase may be chosen to be at a moment during diastole when the regurgitation occurs, such as during the end diastolic phase. The gated image data can then be displayed in order to provide a steadier stream of image frames, in which it may appear as if the leaflets have been immobilized, and to more clearly assess how the regurgitation changes over the course of multiple cardiac cycles.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An apparatus comprising:

one or more processors; and a memory in communication with the one or more processors, wherein the memory contains instructions configured to cause the one or more processors to:

receive, from a first imaging device, first image data of a plurality of image frames of a target heart valve of a subject, wherein the first image data indicates blood flow through the target heart valve, and the first imaging device is one of a trans-esophageal echocardiography (TEE) imaging device or a trans-thoracic echocardiography (TTE) imaging device;

determine, from the first image data, each of a direction and a magnitude of a regurgitant flow through the target valve based on one or more of a jet width, a jet area, or a flow convergence region width;

generate a reference marker in the form of a single arrow indicating each of the direction and magnitude of the regurgitant flow; and output, to one or more image display devices, the first image data and the generated reference marker overlaid over one or more of the image frames in a position and orientation that indicates a position and the direction of the regurgitant flow, wherein the reference marker indicates a range of the regurgitant flow by a width of the arrow.

2. The apparatus of claim 1, wherein the first image data includes color Doppler data, and wherein the instructions are configured to cause the one or more processors to output the first image data without the color Doppler data.

3. The apparatus of claim 1, wherein the instructions are configured to cause the one or more processors to:

receive a user input indicating a desired image output mode from among: color Doppler data without reference markers, reference markers without color Doppler data, or both color Doppler data and reference markers; and output the first image data according to the user input.

4. The apparatus of claim 1, wherein the reference marker indicates the direction of the regurgitant flow by an orientation of the arrow.

5. The apparatus of claim 1, wherein the reference marker indicates the magnitude of the regurgitant flow by one of a color or length of the arrow.

6. An apparatus comprising:

one or more processors; and a memory in communication with the one or more processors, wherein the memory contains instructions configured to cause the one or more processors to:

receive from a first imaging device, first image data of a plurality of image frames of a target heart valve of a subject, wherein the first image data indicates blood flow through the target heart valve, and the first image data is received from a first angle from a trans-esophageal view;

determine, from the first image data, each of a direction and a magnitude of a regurgitant flow through the target valve based on the one or more of a jet width, a jet area, or a flow convergence region width;

generate a first reference marker indicating each of the direction and magnitude of the regurgitant flow;

receive second image data of a target heart valve from a second angle different from the first angle;

register the first image data with the second image data;

generate a second reference marker based on the second image data, wherein the target heart valve is a mitral valve, the second angle is from one of a short-axis base view or a four-chamber view, and the second reference marker is configured to identify at least one of a left atrium, right atrium, superior vena cava, or a height from a transeptal crossing to the mitral valve; and output, to one or more image display devices, a composite image comprising the first image data and the second image data overlaid on one another, with the generated first reference marker displayed in a position and orientation that indicates a position and direction of the regurgitant flow and the generated second reference marker both displayed on the composite image, wherein a position of the second reference marker in the composite image is based on registration of the first image data with the second image data.

7. The apparatus of claim 6, wherein the second reference marker is determined by a machine learning algorithm trained on data from a dataset collected during prior therapeutic procedures.

8. An apparatus comprising:

one or more processors; and a memory in communication with the one or more processors, wherein the memory contains instructions configured to cause the one or more processors to:

receive from a first imaging device, first image data of a plurality of image frames of a target heart valve of a subject, wherein the first image data indicates blood flow through the target heart valve;

determine, from the first image data, each of a direction and a magnitude of a regurgitant flow through the target valve based on the one or more of a jet width, a jet area, or a flow convergence region width;

generate a reference marker indicating each of the direction and magnitude of the regurgitant flow;

wherein the first image data of the target heart valve is within an image plane, and wherein the instructions are configured to cause the one or more processors to, in response to a user input indicating to detect leaflet edges: transmit, to the first imaging device, an instruction to obtain offset image data in an offset image plane parallel to the image plane and offset by a predetermined distance;

receive the offset image data;

detect an edge of a leaflet of the target heart valve from the offset image data;

interpolate, from the offset image data, a position of the edge of the leaflet in the image plane;

generate an edge reference marker indicating the edge of the leaflet in the image plane; and output, to one or more image display devices, the first image data with the generated reference marker displayed in a position and orientation that indicates a position and the direction of the regurgitant flow, and with the generated edge reference marker displayed when the user input indicating to detect leaflet edges is received, wherein a position of the edge reference marker in the first image data corresponds to the interpolated position of the edge of the leaflet.

9. The apparatus of claim 8, wherein the instruction to obtain offset image data instructs the first imaging device to obtain the offset image data on both sides of the image plane, wherein the received offset image data includes first offset image data from an offset plane on a first side of the image plane and second offset image data from an offset plane on an opposite second side of the image plane, and wherein the instructions are configured to cause the one or more processors to interpolate the position of the edge of the leaflet in the image plane based on a combination of the first offset image data and the second offset image data.

10. The apparatus of claim 8, wherein the instructions are configured to cause the one or more processors to:

receive a device user input indicating a device present in the first image data;

select, from a library of computer-generated device models, a model corresponding to the device indicated in the user input;

determine a position, orientation and scaling of the computer-generated device model indicated in the user input based on the first image data; and output, to one or more image display devices, the first image data and the computer-generated device model overlaid over the one or more image frame at the determined position, orientation and scaling.

11. The apparatus of claim 10, wherein the device is a mitral valve clip, and the computer-generated device model of the device is a three-dimensional CAD drawing.

12. The apparatus of claim 8, wherein the instructions are configured to cause the one or more processors to:

receive a puncture device user input indicating a puncture device;

determine, based on prestored puncture height data, a recommended puncture height for the puncture device indicated by the puncture device user input;

generate a puncture reference marker indicating the recommended puncture height based on the prestored puncture height data; and output, to one or more image display devices, the first image data and the puncture reference marker overlaid over the one or more image frames at a location of the recommended puncture.

13. A system, comprising:

the apparatus of claim 8; and a second imaging device, wherein the instructions are configured to cause the one or more processors to:

receive, from the second imaging device, second image data of a plurality of image frames of the target heart valve;

co-register the first image data with the second image data; and output, to the one or more image display devices, at least portions of the first image data and the second image data overlaid on one another in a composite image.

14. The system of claim 13, wherein the one or more image display devices include a first display image device and a second image display device, and wherein the instructions are configured to cause the one or more processors to:

output, to the first image display device, the first image data including the reference marker generated from the first image data; and output, to the second image display device, the second image data and the reference marker generated from the first image data overlaid on the second image data.

15. The system of either one of claim 13 or claim 14, wherein the first imaging device is an echocardiography device, and wherein the second imaging device is one of a fluoroscopy device, a contrast-flow MM device, or a CT device.

16. The apparatus of claim 8, wherein the edge of the leaflet is detected using a machine learning algorithm that detects respective leaflet edges based on information from a predicate patient imaging dataset pool.

17. The apparatus of claim 8, wherein the position of the edge of the leaflet in the image plane is interpolated using a predetermined valve model including structural information about valve morphology.

18. The apparatus of claim 8, wherein acquisition of the offset image data is performed using a gated acquisition scheme such that the offset image data presents the leaflet edges at a common phase of a cardiac cycle.

* * * * *